US012048615B2

(12) United States Patent
Preston

(10) Patent No.: US 12,048,615 B2
(45) Date of Patent: Jul. 30, 2024

(54) DISPOSABLE UNDERGARMENT FASTENING SYSTEM

(71) Applicant: James Preston, Wellston, OH (US)

(72) Inventor: James Preston, Wellston, OH (US)

(*) Notice: Subject to any disclaimer, the term of this patent is extended or adjusted under 35 U.S.C. 154(b) by 531 days.

(21) Appl. No.: 16/359,521

(22) Filed: Mar. 20, 2019

(65) Prior Publication Data

US 2019/0290507 A1 Sep. 26, 2019

Related U.S. Application Data

(60) Provisional application No. 62/646,974, filed on Mar. 23, 2018.

(51) Int. Cl.
*A61F 13/15* (2006.01)
*A61F 13/56* (2006.01)
*A61F 13/62* (2006.01)

(52) U.S. Cl.
CPC ........ *A61F 13/5622* (2013.01); *A61F 13/622* (2013.01); *A61F 2013/5666* (2013.01)

(58) Field of Classification Search
CPC ................ A61F 13/5622; A61F 13/622; A61F 2013/5666
USPC .................... 604/385.03, 386, 387, 394, 396
See application file for complete search history.

(56) References Cited

U.S. PATENT DOCUMENTS 4,662,875 A 5/1987 Hirotsu et al.
4,988,344 A * 1/1991 Reising ................. A61F 13/535 604/358
5,383,871 A 1/1995 Carlin et al.
5,897,546 A 4/1999 Kido et al.
6,045,543 A * 4/2000 Pozniak ............. A61F 13/5633 604/385.01
6,733,483 B2 5/2004 Raufman et al.
7,654,994 B2 2/2010 Winkel et al.
2002/0062117 A1* 5/2002 Raufman ............ A61F 13/5633 604/389

* cited by examiner

*Primary Examiner* — Jacqueline F Stephens
(74) *Attorney, Agent, or Firm* — YORK LAW LLC; Olen L. York, III

(57) ABSTRACT

A disposable undergarment having fastening means comprising a landing area and a pair of fasteners, wherein the landing area and the fasteners include multiple indicia for providing alignment at least in two, bi-directional orientations for horizontal and vertical alignment thereof.

17 Claims, 2 Drawing Sheets

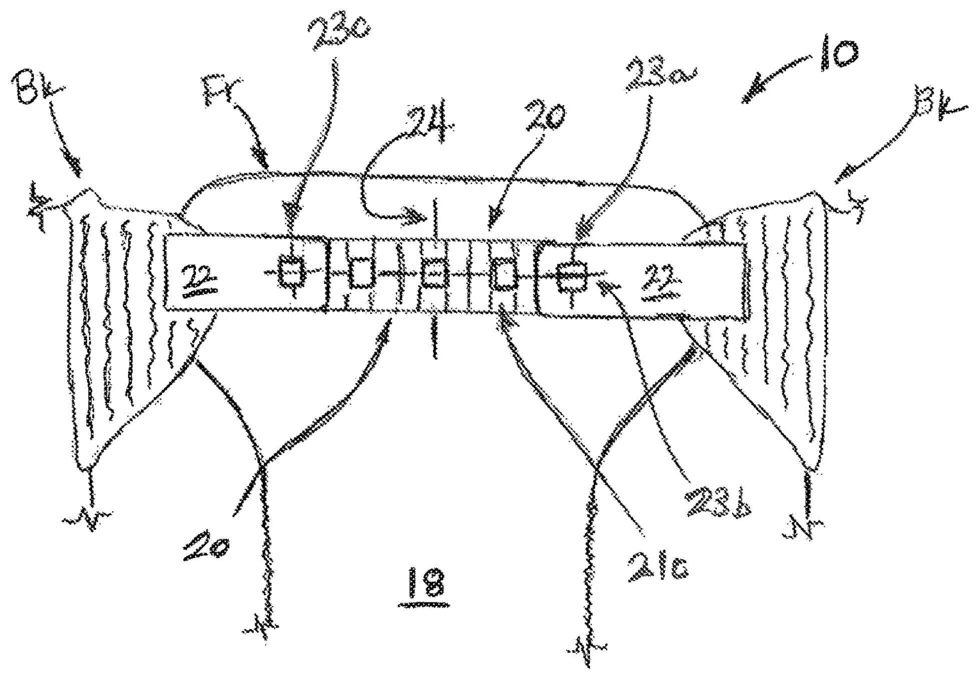
FIG. 3
FIG. 4a
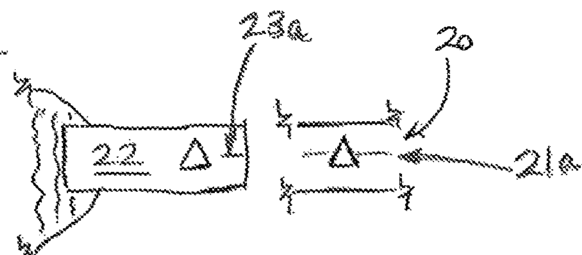
FIG. 4b
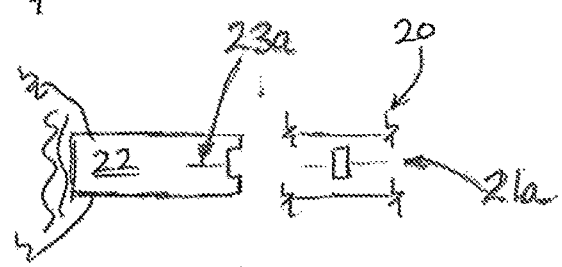
FIG. 4c

DISPOSABLE UNDERGARMENT FASTENING SYSTEM

I. RELATED APPLICATIONS

This application claims the benefit of U.S. Provisional Application No. 62/646,974, filed on Mar. 23, 2018.

II. FIELD OF THE INVENTION

This application discloses claims and embodiments generally related to a disposable undergarment having a fastening system for aligning the disposable undergarment on an individual person or animal's body.

III. BACKGROUND OF THE INVENTION

Disposable absorbent articles generally include fastener tabs for securing the article to a wearer. Proper application and positioning of a disposable diaper is important for the comfort of the wearer but is equally important to the proper functioning of the diaper. Misapplied or ill-fitting diapers can result in gaps or openings about the legs of the wearer. Thus, it is desirable to provide a diaper that may be applied in a comfortable and fully-functioning manner. It is also desirable to provide the person applying the diaper with a simple way to secure the diaper to an individual person or animal.

Several attempts have been made regarding the proper application and fastening of a disposable diaper, such as in U.S. Pat. No. 4,662,875, entitled "Absorbent Article" that discloses a positioning arrangement having indicia on the outer face of the backsheet to aid in properly fitting a disposable diaper to a wearer. The indicia illustrated in that patent include a plurality of parallel, spaced, longitudinally-extending lines and a plurality of dots, each placed on and extending over a portion of the outer surface areas at which the fastener tabs are to be secured.

Thus, it would be desirable to provide an improved disposable diaper.

IV. SUMMARY OF THE INVENTION

In one embodiment, a disposable absorbent undergarment comprises an interior-facing topsheet and an exterior-facing backsheet with an acquisition and distribution layer adjacent the topsheet and an absorbent core adjacent the backsheet. The undergarment also includes a landing area formed on the backsheet, the landing area includes a first right alignment landing guide having a longitudinally-oriented alignment and a second right alignment landing guide having a laterally-oriented alignment, a first left alignment landing guide having a longitudinally-oriented alignment and a second left alignment landing guide having a laterally-oriented alignment. The undergarment also includes a right-fastener and a left-fastener mutually opposed along the lateral margins of the undergarment, each fastener having a first alignment fastener guide and a second alignment fastener guide, wherein the right-fastener first alignment fastener guide is aligned with the first right alignment landing guide and the second right alignment fastener guide is aligned with the second alignment landing guide, and wherein the left-fastener first alignment fastener guide is aligned with the first left alignment landing guide and the second left alignment fastener guide is aligned with the second left alignment landing guide.

The undergarment may further comprise a horizontally-aligned mid-line indicia adjacent either the front margin, the back margin, or both the front margin and the back margin.

The undergarment may further comprise a landing guide having one or more indicia. The indicia may comprise phosphorescent pigment. The indicia may further include a variety of shapes and forms, including various geometric shapes, numbers, letters, lines, and licensed images or symbols.

V. BRIEF DESCRIPTION OF THE DRAWING(S)

The advantages and features of the present invention will become better understood with reference to the following more detailed description and claims taken in conjunction with the accompanying drawings, in which like elements are identified with like symbols, and in which:

FIG. 3 is a plan view of the back of the diaper and the tabs thereon aligned in a longitudinal and lateral orientation along the landing utilizing the indicia provided on the tabs and the landing;

Figure 1:
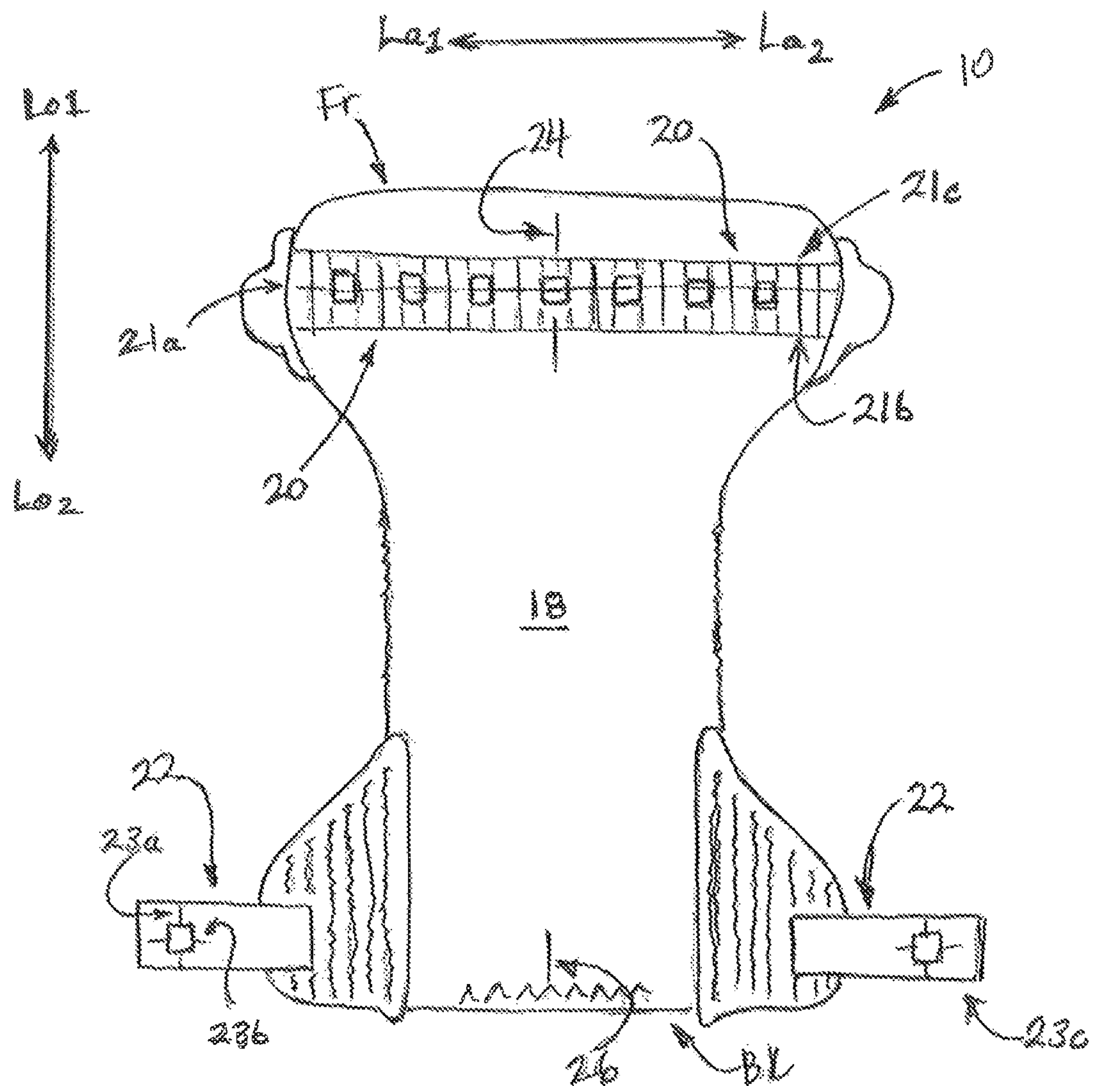
FIG. 1 is a plan view of the exterior surface of a disposable diaper with the front of the diaper at the top of the image and the back of the diaper at the bottom of the image, the view depicting an unassembled diaper with indicia that provides alignment in a longitudinal orientation and in a lateral orientation.

FIG. 4*a* is an alternate embodiment of the right-side tab and right-side of the landing utilizing semi-circular indicia on each for orientation and with a line or hash for additional orientation;

FIG. 4*b* is an alternate embodiment of the right-side tab and right-side of the landing utilizing triangular indicia on each for orientation and with a line or hash for additional orientation; and FIG. 4*c* is an alternate embodiment of the right-side tab and right-side of the landing utilizing rectangular indicia on each for orientation and with a line or hash for additional orientation.

VI. DETAILED DESCRIPTION OF THE EMBODIMENT(S)

It will be readily understood that the components of the present invention, as generally described and illustrated in the figures herein, may be arranged and designed in a wide variety of different configurations. Thus, the following detailed description of the embodiments, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present invention. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

As used herein, an absorbent article or absorbent garment may include incontinence undergarments or incontinence briefs, feminine hygiene articles, undergarments, or briefs, diapers for infants, toddlers, adults, or senior citizens, bandages, and/or other similarly constructed, used, and/or worn article or item intended to absorb human waste and prevent soiling of clothing.

In accordance with the drawings illustrating at least one embodiment, as generally depicted in the drawing figures, an absorbent article and/or garment 10 is illustrated, wherein the article/garment 10 may be described as a diaper for collecting excreted fluid(s) and solid(s) and may be further exemplified as a disposable diaper for an infant, toddler, child, adult, and/or animal.

Figure 2:
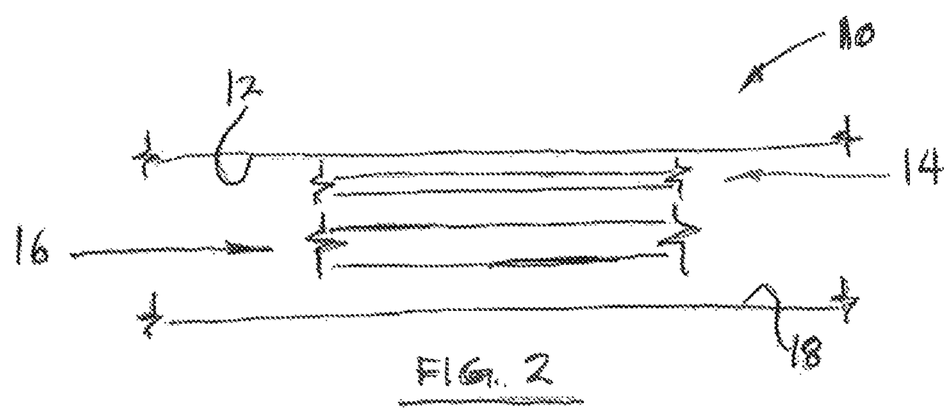
FIG. 2 is a open side-view of the diaper depicting the topsheet and backsheet with the distribution layer and absorbent core orientated therebetween the topsheet and backsheet.

In accordance with at least one embodiment disclosed and depicted herein, consistent with FIGS. 1 through 3, the article 10 comprises a topsheet 12 and a backsheet 18, wherein the topsheet 12 is the interior surface facing and that touches and/or engages the wearer, and wherein the backsheet 18 is the exterior surface that engages clothing and/or the environment. Between sheets 12 and 18 are disposed an acquisition and distribution layer 14 that is adjacent to the topsheet 12 and an absorbent core 16 that is adjacent the backsheet 18. Thus, the topsheet 12 and backsheet 18 sandwich the acquisition/distribution layer 14 and absorbent core 16 therebetween. The backsheet 18 comprises flexible fabric and includes elastic sides and/or cuffing, as well as a landing area or region 20 and fastening ears or tabs 22 (and may be generally referred to as fasteners 22). The landing area or region 20 receives and retains the fasteners 22. The garment 10 may further include a mid-line indicia 24, such as a line placed in a horizontally-oriented position adjacent the landing area 20 at or adjacent the front (Fr) of the undergarment. The garment 10 may further include a corresponding mid-line indicia 26, such as a line placed in a horizontally-oriented position at a mid-point between the right and left fasteners 22 at or adjacent the back (Bk) of the undergarment. Either indicia 24 and/or 26 may be utilized to oriented the article 10 on the individual or animal, whereby the indicia 24 and/or 26 allow for visual alignment of the article 10 near the center of the individual or animal's anatomy.

It is envisioned that the article 10 may comprise at least two general arrangements. In one arrangement, the article 10 is unassembled as an undergarment and opened in a manner that an infant, toddler, child, adult, or animal may be oriented so that the article 10 may be gathered about the individual/animal and then secured along the lower abdomen with semi-permanent adhesive(s) and/or synthetic touch fasteners (e.g., hook-and-loop fasteners). In a second arrangement, the article 10 is assembled and generally defined as an undergarment (mimicking underwear) that may be slid along the legs of the individual/animal and positioned along the crotch/groin region in a manner like underwear or other undergarments. Moreover, additional variations and combinations of such arrangements are contemplated.

Regardless of arrangement, the article 10 will include a landing area 20 and fasteners 22 that provide adjustable positioning of the article 10 along the wearer's crotch/groin and abdominal regions. In an unassembled embodiment, the landing area 20 and fasteners 22 are necessary to secure the article 10 to the individual wearer. In an assembled embodiment, mimicking underwear or other undergarments, the landing area 20 and fasteners 22 provide additional adjustability and fine-tune positioning of the article 10 upon the wearer. For such embodiments, the principles disclosed herein of the cooperation between the landing area 20 and fasteners 22 is generally similar, with any variations or modifications identified and noted below. Thus, it is envisioned that one embodiment may comprise a landing area 20 and fasteners 22, and utilizing front (FR) mid-line indicia 24 as a reference point, with the area to the observer's right of indicia 24 denoted as the right-side and with the area to the observer's left of indicia 24 denoted as the left-side, the landing area 20 includes a first right alignment landing guide **21*a* having a longitudinally-oriented alignment and a second right alignment landing guide 21*b* having a laterally-oriented alignment, and an opposing or mirror-image on the left-side including a first left alignment landing guide 21*a* having a longitudinally-oriented alignment and a second left alignment landing guide 21*b* having a laterally-oriented alignment, and the right fastener 22 and the left fastener 22 each include a first alignment fastener guide 23*a* and a second alignment fastener guide 23*b*. The right-fastener 22 first alignment fastener guide 23*a* is aligned with the first right alignment landing guide 21*a* and the second right alignment fastener guide 23*b* is aligned with the second alignment landing guide 21*b*. Likewise, the left-fastener 22 first alignment fastener guide 23*a* is aligned with the first left alignment landing guide 21*a* and the second left alignment fastener guide 23*b* is aligned with the second left alignment landing guide 21*b*. As is discussed in greater detail below, it is further envisioned that the landing area 20 and fasteners 22 include indicia to provide additional accurate alignment and positioning of the fasteners 22 in relation to the landing area 20. More particularly, it is envisioned that such embodiments may include the use of a variety of indicia that provides multi-directional alignment of the fasteners 22 to the landing area 20**.

For example, the landing area 20 may be described as having a surface with multi-directional aspects, including longitudinal alignment (indicated via bi-directional arrow $Lo_1$ and $Lo_2$) and further including lateral alignment (indicated by bi-directional arrow $La_1$ and $La_2$). The landing area 20 comprises indicia for aligning and placing the fastener(s) 22 in a manner that properly aligns the fastener(s) 22 along longitudinal and lateral alignment.

In one example, consistent with FIG. 1, the landing area 20 comprises separate and independent longitudinal alignment indicia **21*a* and separate and independent lateral indicia 21*b*. In another example, the landing area 20 comprises indicia 21*c* that incorporates and integrates longitudinal indicia and lateral indicia as a unitary whole. In another example, the landing area 20 comprises separate and independent longitudinal indicia 21*a*, lateral indicia 21*b*, and indicia 21*c*** that incorporates additional longitudinal and lateral indicia therein.

In each of these examples, the landing area 20 comprises such indicia (**21*a*, 21*b*, and/or 21*c*) in a manner that is symmetrical and allows for alignment of fasteners 22 that are provided on the right-side and left-side of the disposable undergarment, in mutually opposed positioning and alignment. The use of symmetrical placement of indicia (21*a*, 21*b*, and/or 21*c*), so that the right-side and left-side of the landing area 20 are generally mirror images of one another, and allows the individual placing the disposable undergarment 10 on the wearer to appreciate the preferred alignment of the diaper on wearer. In achieving optimized diaper alignment along the longitudinal alignment and lateral alignment indicia provided on the outer surface of the diaper, application of the diaper in this manner reduces the discomfort of misaligned garments, and further reduces the opportunity for gaps, bunching, or other unwanted misalignment that leads to garment failure and the resultant leakage of bodily fluid or solid that intended to be captured and trapped by the undergarment 10**.

In one specific embodiment, the landing area 20 comprises a separate longitudinal indicia 21*a* and lateral indicia 21*b*, whereby the longitudinal indicia 21*a* may include a dot, a line, a dash, a star, or the like, and the lateral indicia 21*b* may include a separate dot, line, dash, star, or the like. In this embodiment, the indicia 21*a* and 21*b* are not required to match or be the same.

In another specific embodiment, the landing area 20 comprises indicia 21*c* that incorporates and integrates longitudinal indicia 21*a* and lateral indicia 21*b*. Indicia 21*a* and 21*b* may include a geometric form or shape, licensed trademark, licensed copyright, and/or other symbol, device, or the like. As representing but one example, indicia 21*a* and 21*b* are depicted as a square, whereby the horizontally-oriented (and mutually opposed) top and bottom sides of the square serve as the longitudinal indicia 21*a*, and the vertically-oriented (and mutually opposed) lateral sides of the square serve as the lateral indicia 21*b*.

In another specific embodiment, the landing area 20 comprises separate and independent longitudinal indicia 21*a*, lateral indicia 21*b*, and indicia 21*c* that incorporates additional longitudinal indicia and lateral indicia therein. Longitudinal indicia 21*a* may comprise horizontally-oriented indicia (including multiple adjacent horizontal lines or hashing), lateral indicia 21*b* may comprise vertically-oriented indicia (including multiple adjacent vertical lines or hashing), and indicia 21*c* may comprise a two-dimensional geometric form or shape, licensed trademark, licensed copyright, and/or other symbol, device, or the like. As representing but one example, indicia 21*c* is depicted as a square. The right fastener 22 and the left fastener 22 will include complementary indicia 23*a*-23*c* that generally matches and aligns with the indicia 21*a*-21*c* provided on the landing area 20. It is further envisioned that one or more of the indicia 23*a*-23*c* that may be utilized and included on the fastener(s) 22 may include voids cut and removed therefrom that have the shape and/or form of the indicia 21*a*-21*c* disposed on the landing area 20, thereby allowing the void to display the underlying landing area 20 indicia 21*a*-21*c* therethrough for alignment purposes.

As depicted in FIG. 1 and FIG. 3, and as but one example, the longitudinal alignment indicia (21*a* and 23*a*) are horizontally-oriented lines or hashes, and the lateral alignment indicia (21*b* and 23*b*) are vertically-oriented lines or hashes. In an embodiment with a combination of longitudinal and lateral alignment indicia (21*c* and 23*c*), horizontal and vertically-oriented lines or hashes are envisioned as one example thereof.

FIGS. 4*a* through 4*c* illustrate and disclose a non-exhaustive variety of geometries and/or indicia that may be utilized for longitudinal and/or lateral alignment of the fastener(s) 22 on the landing area 20. For example, FIG. 4*a* depicts a fastener 22 having two semi-circular voids formed therethrough that may be aligned with two semi-circular indicia formed on the landing area 20. Similarly, FIG. 4*b* depicts a fastener 22 having a triangular void formed therethrough that may be aligned with a triangular-shaped indicia formed on the landing area 20. Likewise, FIG. 4*c* depicts a fastener 22 having a rectangular void formed therethrough that may be aligned with a rectangular-shaped indicia formed on the landing area 20. In each of FIGS. 4*a* through 4*c*, the depicted voids represent the fastener indicia 21*a* and landing indicia 23*a* generally used for lateral alignment thereof, while the horizontally-oriented lines represent the fastener indicia 21*b* and landing indicia 23*b* generally used for longitudinal alignment thereof.

FIGS. 4*a* through 4*c* represents only a few of the geometric forms or shapes that may be utilized. It is envisioned that one or more variously sized circles, multi-sided and/or polygonal shapes (e.g., triangles, squares, rectangles, pentagonals, hexaongals, and the like), and other symbols (such as licensed logos and/or trademarks).

It is envisioned that the indicia 21*a*-21*c* and/or indicia 23*a*-23*c* may include phosphorescent pigment(s) impregnated into the fabric of the garment. It is intended that the phosphorescent pigment(s) will assist in the placement of the garment by illuminating the indicia 21*a*-21*c* and/or 23*a*-23*c* in darkened environments and assisting with aligning the individual elements of the fastening system, and especially aligning the indicia 21*a*, 21*b*, and/or 21*c* with indicia 23*a*, 23*b*, and/or 23*c*, as appropriate.

It is to be understood that the embodiments and claims are not limited in its application to the details of construction and arrangement of the components set forth in the description and illustrated in the drawings. Rather, the description and the drawings provide examples of the embodiments envisioned, but the claims are limited to the specific embodiments. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the U.S. Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. It is intended that the application is defined by the claims appended hereto.

What is claimed is:

1. A disposable absorbent undergarment comprising:

an interior-facing topsheet and an exterior-facing backsheet;

an acquisition and distribution layer adjacent the topsheet;

an absorbent core adjacent the backsheet;

a landing area formed on the backsheet, the landing area including:

a first right alignment landing guide disposed on the right-side of the landing area and having a longitudinally-oriented alignment and a second right alignment landing guide disposed on the right-side of the landing area having a laterally-oriented alignment;

a first left alignment landing guide disposed on the left-side of the landing area and having a longitudinally-oriented alignment and a second left alignment landing guide disposed on the left-side of the landing area and having a laterally-oriented alignment;

an intermediate indicia disposed adjacent the landing area and disposed intermediately between the right alignment guides and the left alignment guides, the intermediate indicia comprising a line having a horizontal orientation so that the terminuses of the line are disposed north-to-south for visual alignment of the undergarment relative to the center of the user's anatomy;

a right-fastener and a left-fastener mutually opposed along the lateral margins of the undergarment, each fastener having a first alignment fastener guide and a second alignment fastener guide, wherein the right-fastener first alignment fastener guide is aligned with the first right alignment landing guide and the second right alignment fastener guide is aligned with the second alignment landing guide, and wherein the left-fastener first alignment fastener guide is aligned with the first left alignment landing guide and the second left alignment fastener guide is aligned with the second left alignment landing guide; and, wherein the landing area comprises indicia and multiple alignment guides, the indicia for properly aligning the undergarment with an individual's anatomy and the multiple alignment guides for properly aligning the right-fastener and the left-fastener with the multi-directional guides for proper longitudinal and lateral orientations.

2. The undergarment of claim 1 further comprising a second intermediate indicia formed adjacent the landing area, the second intermediate indicia comprising a horizontally-oriented line for visual alignment of the undergarment relative to the center of the user's anatomy.

3. The undergarment of claim 1, wherein the landing guides comprising the first right alignment landing guide, the second right alignment landing guide, the first left alignment landing guide, and the second left alignment landing guide each comprise indicia.

4. The undergarment of claim 3, wherein:

the first right alignment landing guide and the first left alignment landing guide comprise the same indicia; and the second right alignment landing guide and the second left alignment landing guide comprise the same indicia.

5. The undergarment of claim 4, wherein the first right alignment landing guide and the first left alignment landing guide comprise phosphorescent pigment.

6. The undergarment of claim 4, wherein the second right alignment landing guide and the second left alignment landing guide comprise phosphorescent pigment.

7. The undergarment of claim 3, wherein the indicia comprise a geometric shape.

8. The undergarment of claim 3, wherein the indicia comprise alpha-numeric characters.

9. The undergarment of claim 3, wherein the indicia comprise a licensed image.

10. A disposable absorbent undergarment comprising:

an interior-facing topsheet and an exterior-facing backsheet;

an acquisition and distribution layer adjacent the topsheet;

an absorbent core adjacent the backsheet;

the topsheet and backsheet mutually joined along the exterior margin to form an undergarment having a front margin and a back margin in mutual opposition before application to a wearer;

a landing area formed on the backsheet, the landing area including:

a first right alignment landing guide disposed on the right-side of the landing area and having a longitudinally-oriented alignment and a second right alignment landing guide disposed on the right-side of the landing area having a laterally-oriented alignment;

a first left alignment landing guide disposed on the left-side of the landing area and having a longitudinally-oriented alignment and a second left alignment landing guide disposed on the left-side of the landing area and having a laterally-oriented alignment;

an intermediate indicia disposed adjacent the landing area and disposed intermediately between the right alignment guides and the left alignment guides, the intermediate indicia comprising a line having a horizontal orientation so that the terminuses of the line are disposed north-to-south for visual alignment of the undergarment relative to the center of the user's anatomy;

a right-fastener and a left-fastener mutually opposed along the lateral margins of the undergarment, each fastener having a first alignment fastener guide and a second alignment fastener guide, wherein the right-fastener first alignment fastener guide is aligned with the first right alignment landing guide and the second right alignment fastener guide is aligned with the second alignment landing guide, and wherein the left-fastener first alignment fastener guide is aligned with the first left alignment landing guide and the second left alignment fastener guide is aligned with the second left alignment landing guide;

the right-fastener and the left-fastener applied to the landing area to join the back margin to the front margin to assemble the undergarment about the wearer; and, wherein the landing area comprises indicia and multiple alignment guides, the indicia for properly aligning the undergarment with an individual's anatomy and the multiple alignment guides for properly aligning the right-fastener and the left-fastener with the multi-directional guides for proper longitudinal and lateral orientations.

11. The undergarment of claim 10 further comprising a second intermediate indicia formed adjacent the landing area, the second intermediate indicia comprising a horizontally-oriented line for visual alignment of the undergarment relative to the center of the user's anatomy.

12. The undergarment of claim 10, wherein the landing guides comprising the first right alignment landing guide, the second right alignment landing guide, the first left alignment landing guide, and the second left alignment landing guide each comprise indicia.

13. The undergarment of claim 12, wherein:

the first right alignment landing guide and the first left alignment landing guide comprise the same indicia; and the second right alignment landing guide and the second left alignment landing guide comprise the same indicia.

14. The undergarment of claim 13, wherein the indicia of the landing guide comprise phosphorescent pigment.

15. The undergarment of claim 12, wherein the indicia comprise a geometric shape.

16. The undergarment of claim 12, wherein the indicia comprise alpha-numeric characters.

17. The undergarment of claim 12, wherein the indicia comprise a licensed image.

* * * * *